United States Patent
Kanemaru et al.

(10) Patent No.: US 8,774,352 B2
(45) Date of Patent: Jul. 8, 2014

(54) X-RAY CT APPARATUS

(75) Inventors: Takashi Kanemaru, Nasushiobara (JP); Keiji Matsuda, Nasushiobara (JP); Hiroyuki Ooishi, Otawara (JP); Michito Nakayama, Utsunomiya (JP); Machiko Iso, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 222 days.

(21) Appl. No.: 13/187,058

(22) Filed: Jul. 20, 2011

(65) Prior Publication Data
US 2012/0020453 A1 Jan. 26, 2012

(30) Foreign Application Priority Data
Jul. 22, 2010 (JP) .................. 2010-164508

(51) Int. Cl.
A61B 6/03 (2006.01)
(52) U.S. Cl.
USPC .......................................................... 378/15
(58) Field of Classification Search
USPC ................ 378/4, 15, 19, 141, 199, 200
See application file for complete search history.

(56) References Cited

U.S. PATENT DOCUMENTS

| 6,909,775 | B2 * | 6/2005 | Ray et al. ........... | 378/141 |
| 7,201,515 | B2 * | 4/2007 | Lacey ................ | 378/199 |
| 2007/0098137 | A1 | 5/2007 | Joshi et al. | |
| 2009/0279660 | A1 * | 11/2009 | Takamatsu et al. ...... | 378/19 |

FOREIGN PATENT DOCUMENTS

| CN | 1752881 A | 3/2006 |
| CN | 101116620 A | 2/2008 |
| JP | 2000-037374 A | 2/2000 |
| JP | 2000-342568 A | 12/2000 |
| JP | 2002-202377 A | 7/2002 |
| JP | 2005-99674 | 4/2005 |
| JP | 2007-260092 | 10/2007 |
| JP | 2009-268830 A | 11/2009 |
| JP | 2009-273781 | 11/2009 |
| JP | 2010-237543 | 10/2010 |

OTHER PUBLICATIONS

Chinese Office Action Issued Sep. 13, 2012 in Patent Application No. 201110205842.7.
Office Action issued Mar. 11, 2014 in Japanese Patent Application No. 2010-164508 filed Jul. 22, 2010.

* cited by examiner

Primary Examiner — Irakli Kiknadze
(74) Attorney, Agent, or Firm — Oblon, Spivak, McClelland, Maier & Neustadt, L.L.P.

(57) ABSTRACT

An X-ray CT apparatus according to the embodiments has a rotation base that includes a plurality of units, including an X-ray generator that irradiates a subject with X-rays, and an X-ray detector that detects X-rays transmitted through the subject. It also has a pathway that communicates between the X-ray detector and at least one other unit excluding the X-ray generator and the X-ray detector. It also has an air supplier that supplies air in the other units to the X-ray detector via the pathway. It also has a temperature measuring part that measures the temperature in the X-ray detector. It also has a controller that performs control of the air supplier based on the measured result from the temperature measuring part.

6 Claims, 12 Drawing Sheets

X-RAY CT APPARATUS

CROSS-REFERENCE TO RELATED APPLICATION

This application is based upon and claims the benefit of priority from Japanese Patent Application No. 2010-164508, filed Jul. 22, 2010; the entire contents of which are incorporated herein by reference.

FIELD

Embodiments of the present invention relate to an X-ray CT apparatus.

BACKGROUND

An X-ray CT apparatus is an image diagnosis apparatus that radiates X-rays, detects X-rays transmitted through a subject, and reconstructs an image inside the subject from the projection data indicating the intensity of the detected X-rays.

This system radiates X-rays around the subject from multiple directions, performs scanning by 360°, for example, and obtains projection data. From this projection data, one tomographic view can be reconstructed. Moreover, it is possible to move the scanning position continuously in the direction of the subject's body axis and obtain a plurality of sets of projection data. Alternatively, if a so-called multi-row detector CT having a plurality of X-ray detectors is used, it is possible to obtain a plurality of sets of projection data simultaneously. Based on that plurality of sets of projection data, a volume image, which is a three-dimensional image, can be reconstructed.

Obtaining the projection data is performed with an X-ray detector that has an X-ray detecting element. Because detection sensitivity of the X-ray detecting element depends on temperature, it is desirable for the temperature of the X-ray detector to be maintained constant (for example, approximately 25±1° C.).

Therefore, it is common to install a warming means such as a heater in the X-ray detector to make temperature adjustments.

DETAILED DESCRIPTION

An X-ray CT apparatus according to the embodiments has a rotation base that includes a plurality of units, including an X-ray generator that irradiates a subject with X-rays, and an X-ray detector that detects X-rays transmitted through the subject. It also has a pathway that communicates between the X-ray detector and at least one other unit excluding the X-ray generator and X-ray detector. It also has an air supplier that supplies air in other units to the X-ray detector via the pathway. It also has a temperature measuring part that measures the temperature in the X-ray detector. It also has a controller that performs control of the air supplier based on the measured result from the temperature measuring part.

[Configuration]

First, the configuration of the X-ray CT apparatus that is common to the first through fourth embodiments is described.

Figure 1:
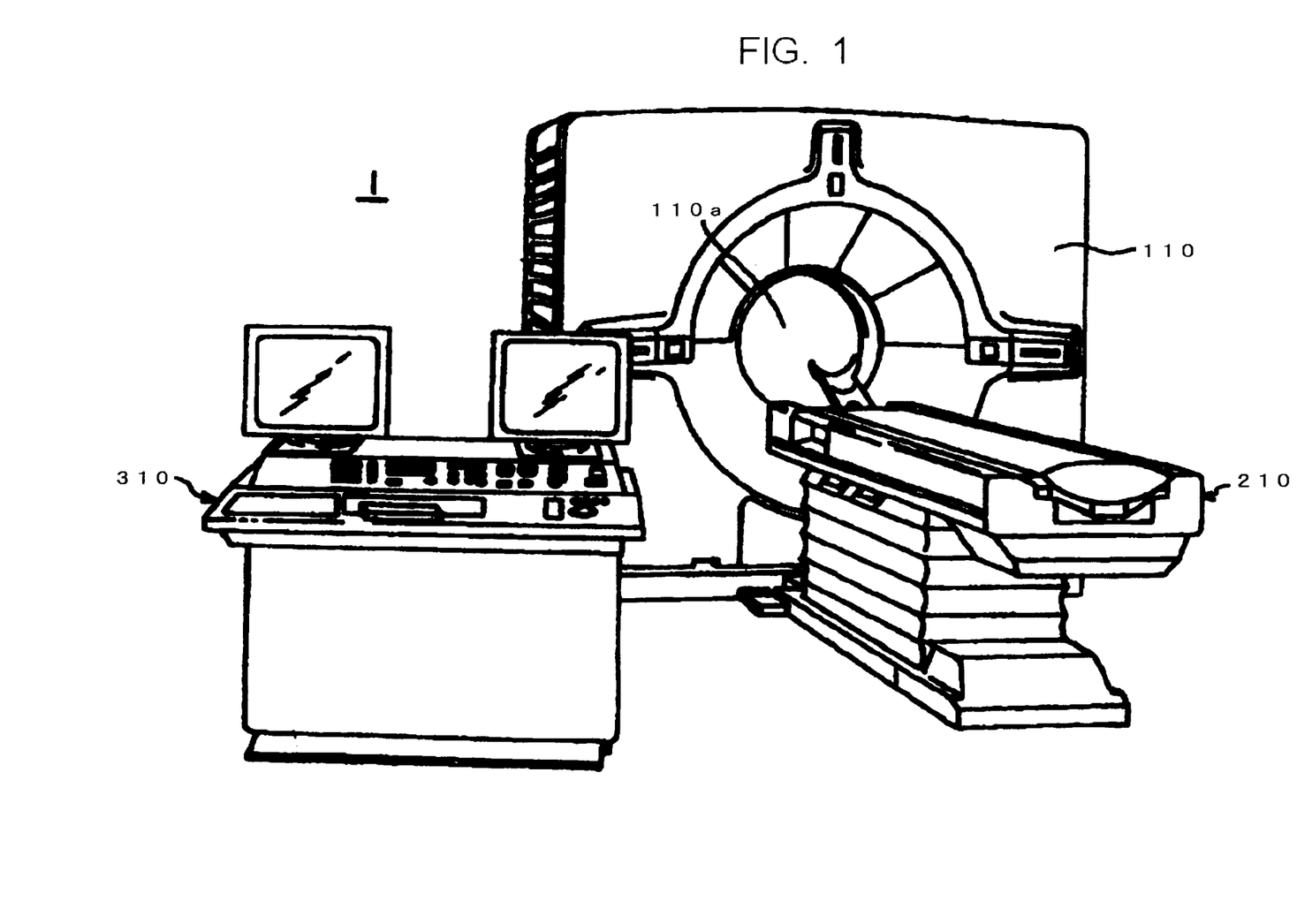
FIG. 1 is a diagram showing the appearance of an X-ray CT apparatus according to embodiments.

FIG. 1 is a diagram showing the appearance of the X-ray CT apparatus. The X-ray CT apparatus 1 is an image diagnosis apparatus that radiates X-rays, detects transmission through a subject, and reconstructs an image of the subject from the projection data indicating the intensity of the detected X-rays. This X-ray CT apparatus 1 comprises a gantry apparatus 110, a bed 210, and a console 310.

The gantry apparatus 110 radiates X-rays and detects X-rays transmitted through the subject. An opening 110a is formed in the center of the gantry apparatus 110. The bed 210 inserts the subject lying on a table-top 212 that will be described later into the opening 110a. The X-ray detection data detected by the gantry apparatus 110 is input into the console 310. The console 310 processes the detected data to reconstruct an image of the subject.

Figure 2:
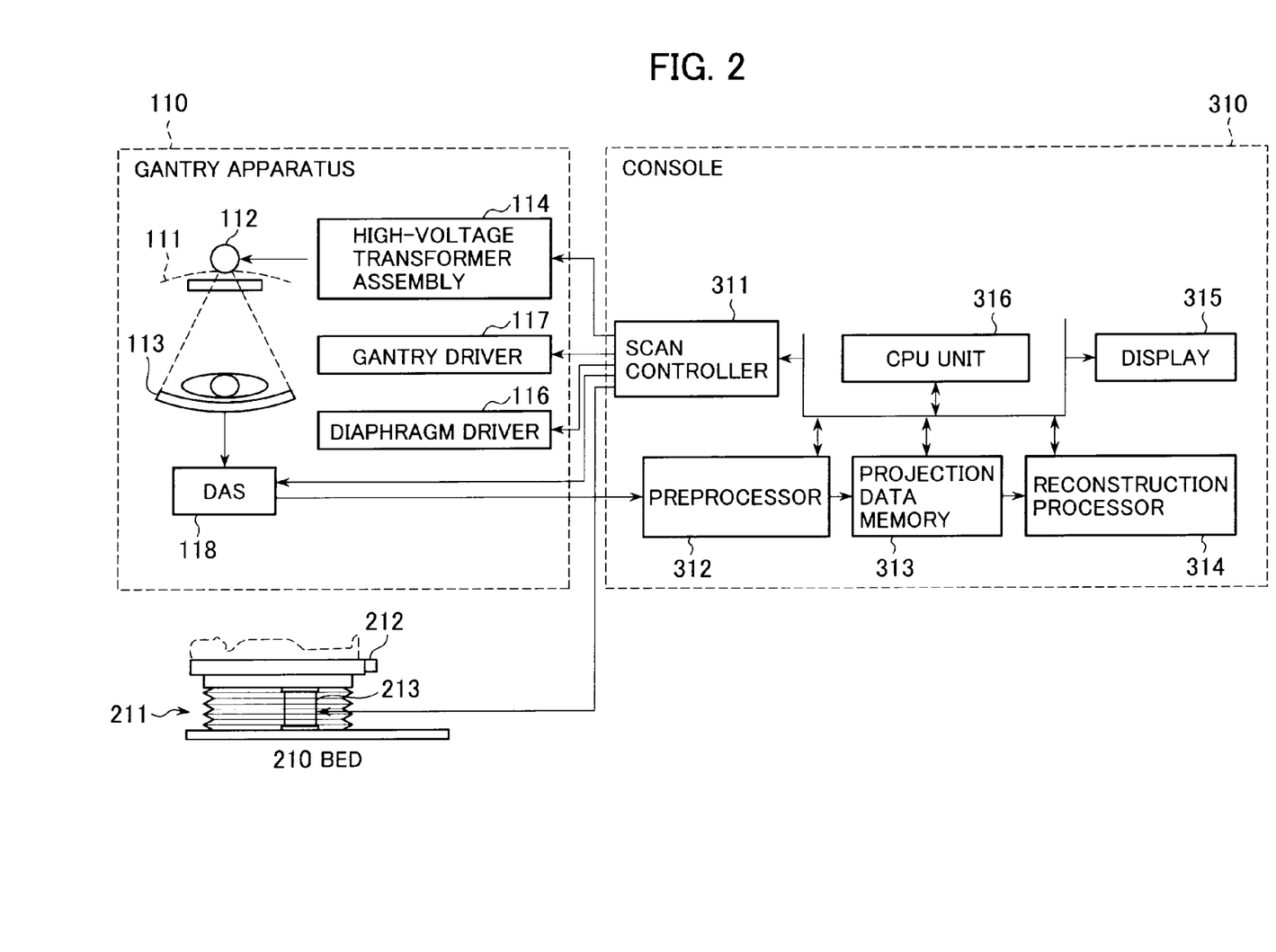
FIG. 2 is a block diagram showing the configuration of the X-ray CT apparatus according to the embodiments.

FIG. 2 is a block diagram showing the configuration of the X-ray CT apparatus 1. Within the gantry apparatus 110, a rotation base 111 is housed. In the rotation base 111, the X-ray generator 112 and the X-ray detector 113 are housed in an opposing manner. Moreover, within the gantry apparatus 110, a high-voltage transformer assembly 114 that generates high voltage to be applied to the X-ray generator 112, a diaphragm driver 116 that drives a X-ray diaphragm 115, a gantry driver 117 that drives the rotation base 111, and a DAS (data acquisition system) 118 that acquires the detection result from the X-ray detector 113 are disposed.

The rotation base 111 responds to the drive of the gantry driver 117 to rotate around the opening 110a. The X-ray generator 112 receives supply of filament heating current and application of high voltage from the high-voltage transformer assembly 114 to generate X-rays.

The X-ray detector 113 includes multi-row and multichannel X-ray detecting elements 113a and detects X-rays transmitted through the subject, outputting the detected data as current signals.

The X-ray diaphragm 115 has a configuration for focusing X-rays generated by the X-ray generator 112 into a fan beam shape or a cone beam shape.

The diaphragm driver 116 drives X-ray diaphragm 115 so that X-rays generated at the X-ray generator 112 forms a predefined shape.

The DAS 118 converts the current signal from each X-ray detecting element into a voltage signal, and periodically integrates and amplifies this voltage signal to convert it into a digital signal.

Moreover, the DAS 118 outputs the detected data converted into the digital signal to the console 310.

The table-top 212 is mounted on the bed base 211 of the bed 210. The table-top 212 is movable relative to the opening 110a at a predefined speed, in response to the drive of a bed driver 213.

The console 310 comprises a scan controller 311, a preprocessor 312, a projection data memory 313, a reconstruction processor 314, a display 315, and a CPU unit 316.

The CPU unit 316 is a computer comprising an arithmetic controller, a main memory, and an external memory. The CPU unit 316 creates control information from imaging conditions to send it to the scan controller 311, the preprocessor 312, the projection data memory 313, the reconstruction processor 314, and the display 315.

The scan controller 311 outputs a drive signal to the high-voltage transformer assembly 114, the gantry driver 117, the DAS 118, the diaphragm driver 116, and the bed driver 213 according to the control information. With the drive signal output to the gantry driver 117 and the bed driver 213, the pair of the X-ray generator 112 and the X-ray detector 113, and the table-top 212 make relative movements in a helical manner (helical scanning).

The preprocessor 312 performs sensitivity correction that corrects the intensity of X-rays on the detected data, and outputs projection data to the projection data memory 313. The projection data memory 313 temporarily stores the projection data.

The reconstruction processor 314 reads out the projection data stored in the projection data memory 313 and reconstructs the image of the subject. As reconstruction processing, any method such as two-dimensional Fourier transform, for example, can be employed.

The image of the subject reconstructed by the reconstruction processor 314 is output to the display 315 via the CPU unit 316.

Figure 3:
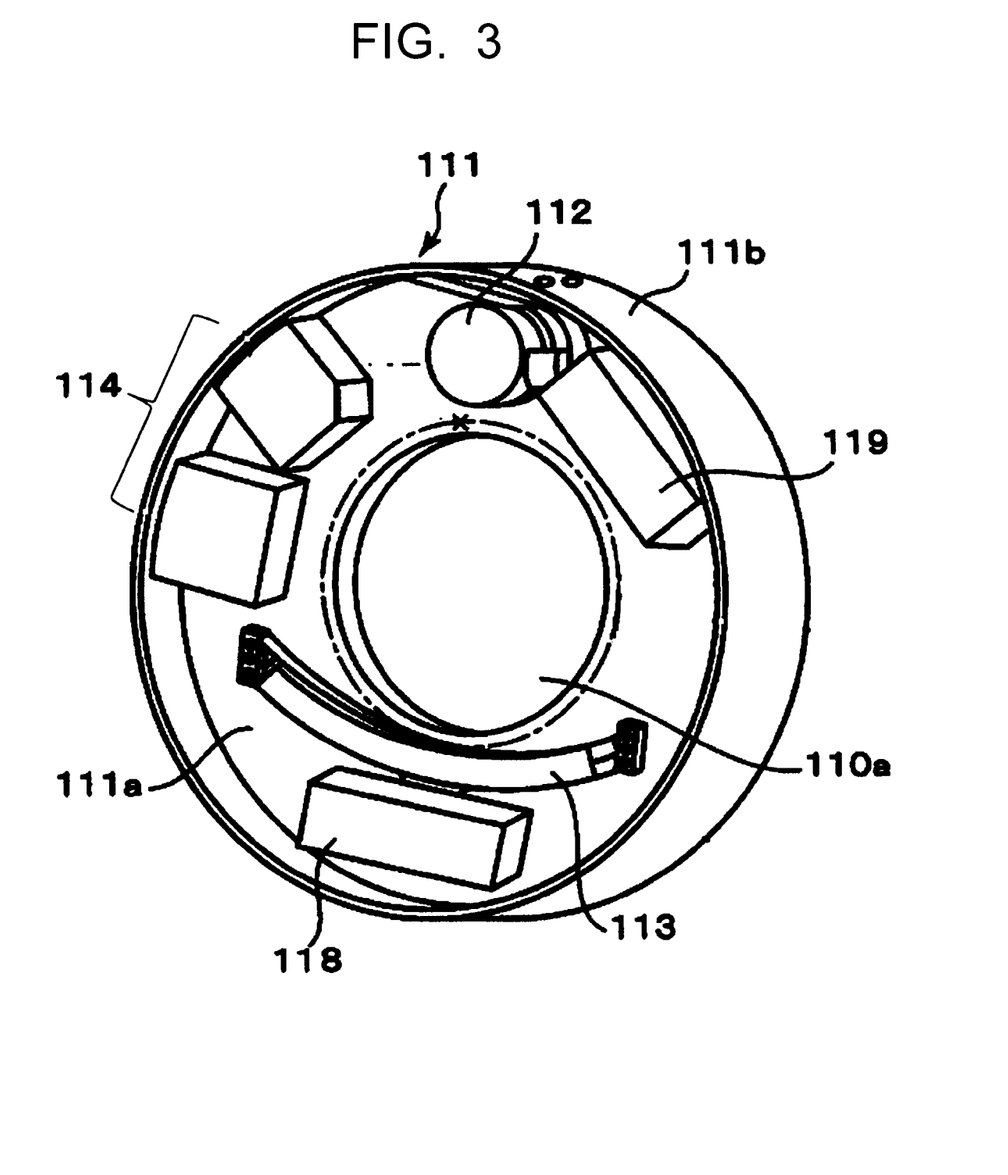
FIG. 3 is a perspective view showing a rotation base of the X-ray CT apparatus according to the embodiments.

FIG. 3 is a perspective view showing the detail of rotation base 111 in such an X-ray CT apparatus 1. The rotation base 111 is formed from a flat plane part 111a and a drum part 111b.

The flat plane part 111a stands along the aperture plane of the opening 110a and has a ring shape that is concentric with the opening 110a. The flat plane part 111a rotates around the same axis as the opening 110a. The drum part 111b is joined to an outer perimeter of the flat plane part 111a and has a shape excluding both end faces of a cylindrical shape. The drum part 111b stands across both front and back faces of the flat plane part 111a.

Attached to this rotation base 111 are units such as the X-ray generator 112, the X-ray detector 113, the high-voltage transformer assembly 114, the DAS 118, and the cooling part 119.

The high-voltage transformer assembly 114 has a function to supply the X-ray generator 112 with high voltage. Moreover, the cooling part 119 has a function to cool the X-ray generator 112.

In addition, in FIG. 2 and FIG. 3, some configurations such as a pathway 120 and an air supplier 121, which will be described later, are omitted.

[The First Embodiment]

Figure 4:
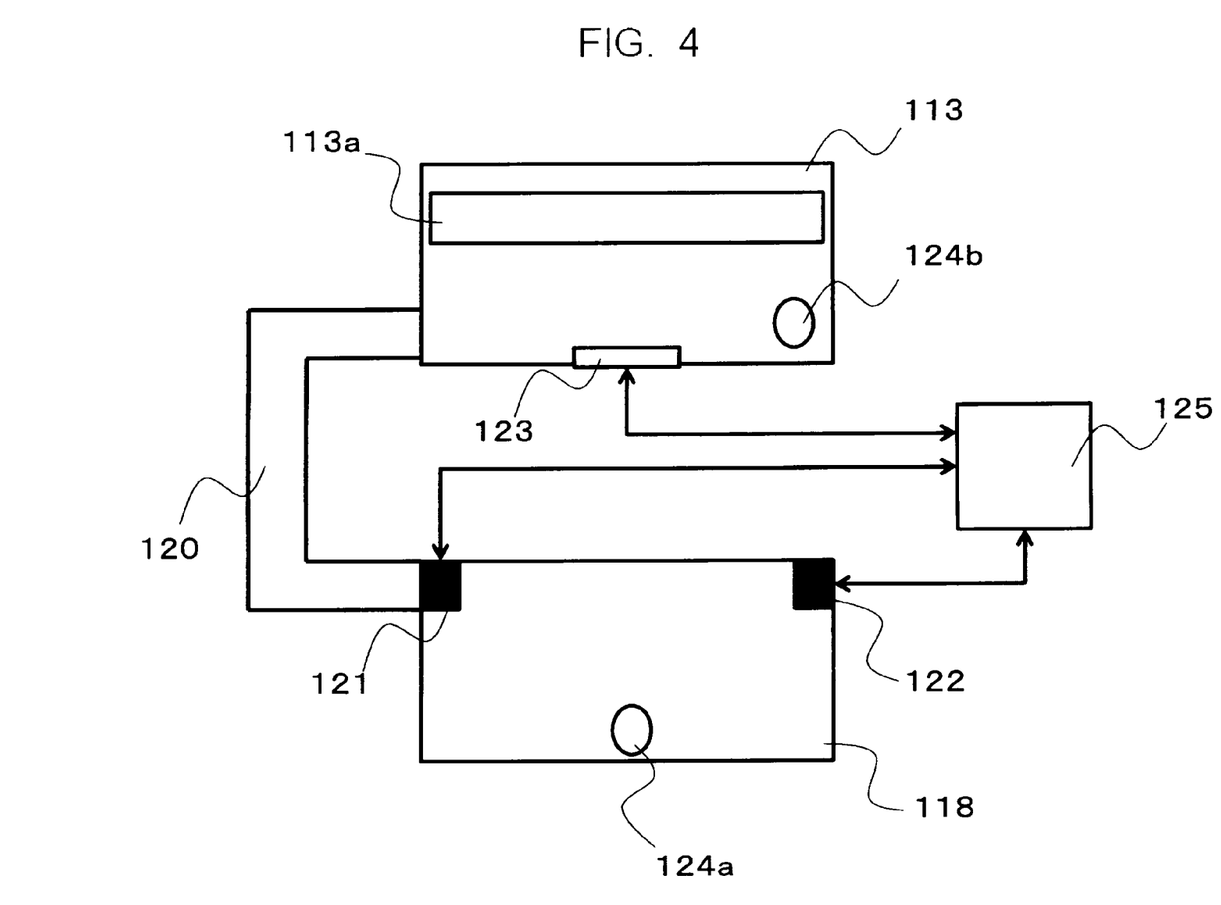
FIG. 4 is a block diagram showing the relation between components of the X-ray CT apparatus according to the first embodiment.
Figure 5:
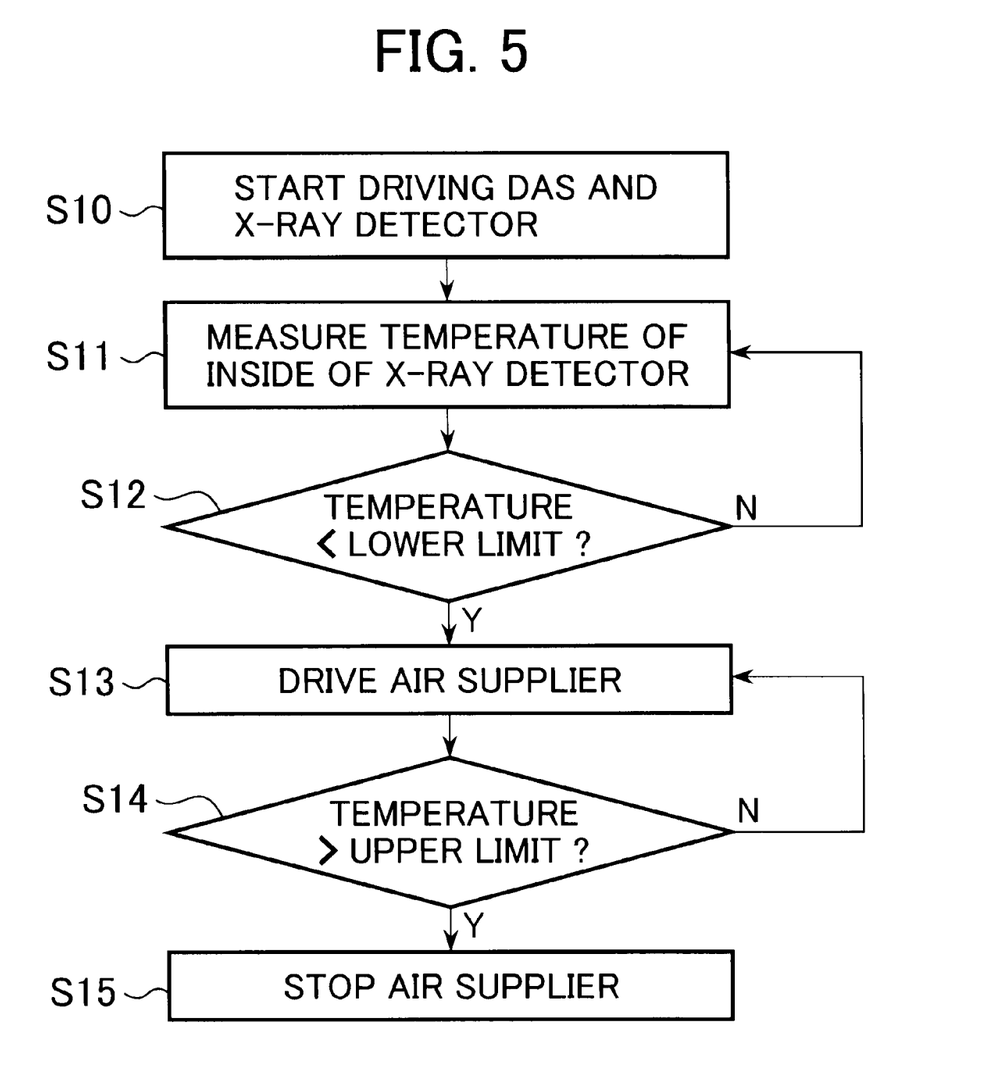
FIG. 5 is a flowchart showing an overview of a processing according to the first embodiment.

Next, using FIGS. 4 and 5, the first embodiment is described.

As shown in FIG. 4, in this embodiment, a pathway 120, an air supplier 121, an air regulator 122, a temperature measuring part 123, a vent 124a, a vent 124b, and a controller 125 are installed.

The pathway 120 is configured to communicate between the X-ray detector 113 and the DAS 118, and is capable of leading the air from the DAS 118 to the X-ray detector 113.

The air supplier 121 installed in the DAS 118 has a function to supply the air in the DAS 118 to the X-ray detector 113 via the pathway 120. This air supplier 121 is configured so that it can supply air, such as a fan or pump, for example.

In addition, the air supplier 121 is only needed to have the function to supply the air in the DAS 118 to the X-ray detector 113.

Therefore, the air supplier 121 need not be installed in the DAS 118, and for example, may be installed in the pathway 120.

The air regulator 122 installed in the DAS 118 has a function to exhaust the air in the DAS 118 out of the DAS 118 and inspire the air outside the DAS 118 into the DAS 118. For example, when the air in the DAS 118 reaches a high temperature, the air supplier 121 supplies a portion thereof to the X-ray detector 113, and also the air regulator 122 exhausts the air in the DAS 118 out of the DAS 118. In addition, the air regulator 122 is not a configuration essential to this embodiment.

The temperature measuring part 123 installed in the X-ray detector 113 has a function to measure the temperature in the X-ray detector 113.

The vent 124a installed in the DAS 118 and the vent 124b installed in the X-ray detector 113 are through-holes installed in order to inspire the air outside the DAS 118 and outside the X-ray detector 113 into the DAS 118 and into the X-ray detector 113. The vent 124a and the vent 124b are also through-holes installed in order to exhaust the air in the DAS 118 and in the X-ray detector 113 out of the DAS 118 and out of the X-ray detector 113. For example, if the air in the DAS 118 is supplied to the X-ray detector 113 by driving the air supplier 121, the vent 124a plays a role as an inspiration port that introduce the air outside the DAS 118 into the DAS 118. Moreover, in that case, the vent 124b plays a role as an exhaust port for distributing the air from the DAS 118 into the X-ray detector 113.

The controller 125 is installed, for example, in the rotation base 111. The controller 125 performs control of the air supplier 121, the air regulator 122, the temperature measuring part 123, etc. In addition, it is possible that the CPU unit 316 is configured to have the function of the controller 125.

Next, using FIG. 5, the operation of this embodiment is described in detail.

First, in conjunction with use of the X-ray CT apparatus, the X-ray detector 113 and the DAS 118 start to operate (S10).

The DAS 118 radiates heat as it is driven. The air in the DAS 118 is warmed with this heat.

On the other hand, in conjunction with the operation of the X-ray detector 113, the temperature measuring part 123 starts to measure the temperature in the X-ray detector 113 (S11). The temperature measuring part 123, for example, performs measurements at predetermined time intervals.

Here, if the measured temperature by the temperature measuring part 123 is below the lower limit (for example, 24° C.) (that is, if it is "Y" at S12), the controller 125 sends a drive signal to the air supplier 121.

Based on this drive signal, the air supplier 121 supplies the warmed air in the DAS 118 to the X-ray detector 113 via the pathway 120 (S13).

If the measured temperature by the temperature measuring part 123 is equal to or above the lower limit (that is, if it is "N" at S12), no drive signal is sent to the air supplier 121 by the controller 125.

Under the state in which the air supplier 121 is driven and the warmed air in the DAS 118 is supplied into the X-ray detector 113 at S13, if the measured temperature by the temperature measuring part 123 exceeds the upper limit (that is, if it is "Y" at S14), the controller 125 sends a stop drive signal to the air supplier 121.

In addition, if the measured temperature at the temperature measuring part 123 does not exceed the upper limit (that is, if it is "N" at S14), no stop drive signal is sent to the air supplier 121 by the controller 125.

Based on this stop drive signal, the air supplier 121 stops the operation to supply air to the X-ray detector 113 (S15). In addition, when the air supplier 121 is formed with a fan, for example, it is also possible to allow such an operation as reducing the rotation speed of the fan instead of completely stopping its operation.

As above, according to this embodiment, without installing a warming means such as a heater in the X-ray detector 113, the air warmed in the DAS 118 allows temperature control in the X-ray detector 113. Therefore, no noise is added to the detection result from the X-ray detector 113 due to the effect of electromagnetic waves generated by the operation of the warming means. That is, the image quality of tomographic images and volume images formed using that detection result is not affected.

[The Second Embodiment]

Figure 6:
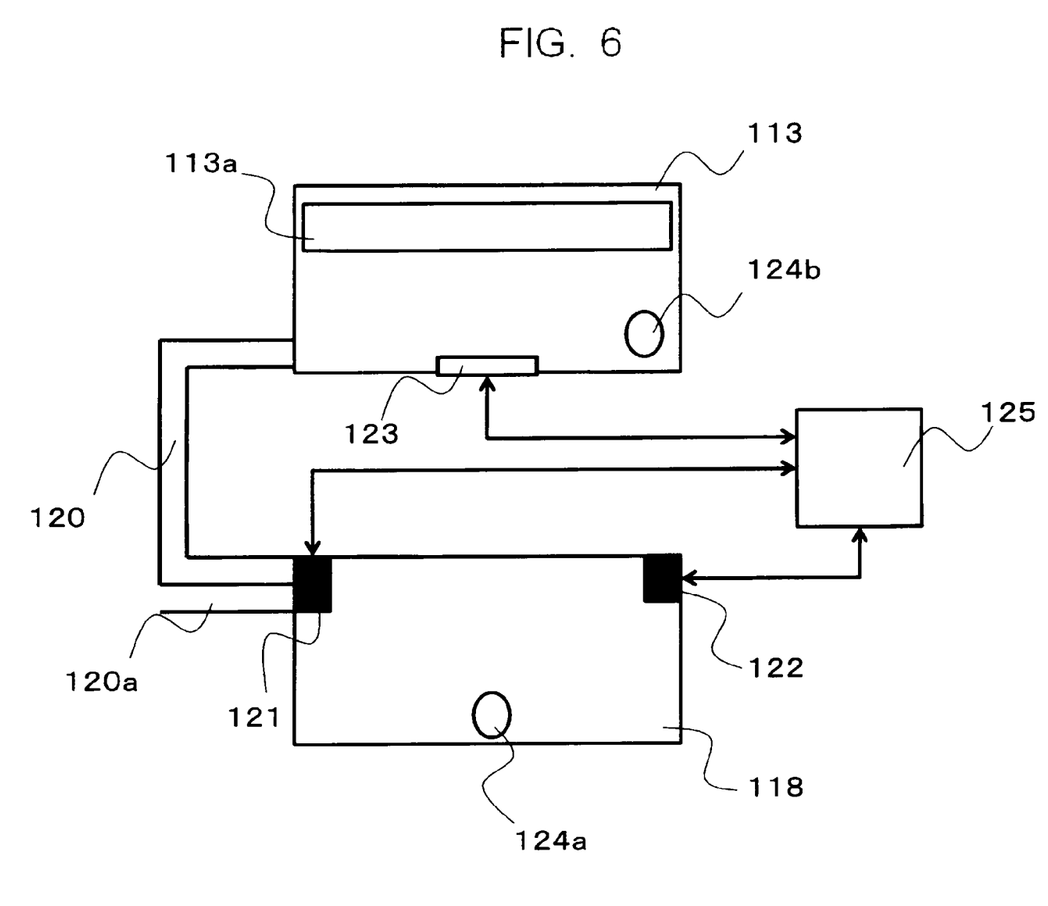
FIG. 6 is a block diagram showing the relation between components of the X-ray CT apparatus according to the second embodiment.
Figure 7:
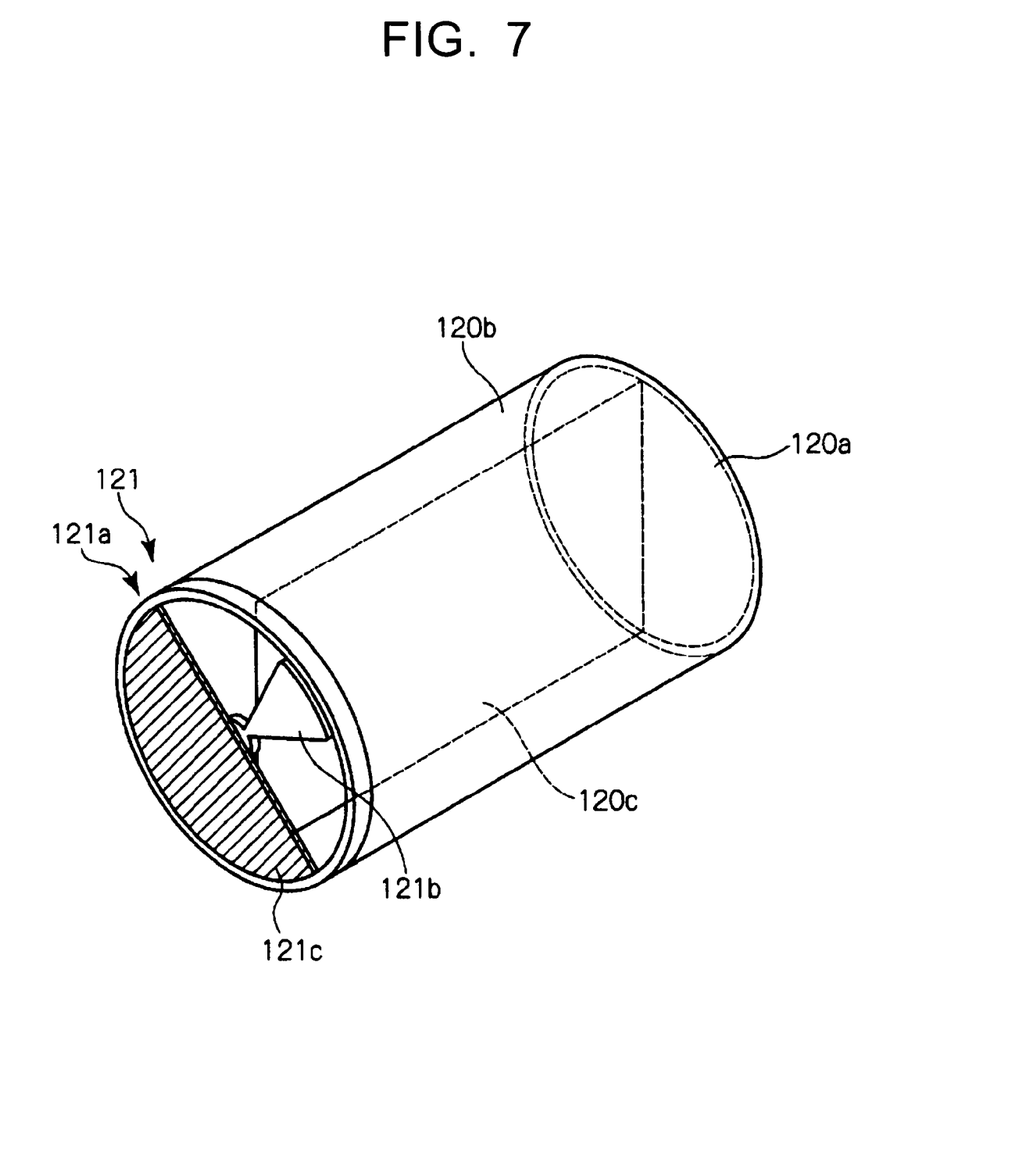
FIG. 7 is an enlarged view of an air supplier according to the second embodiment.
Figure 8:
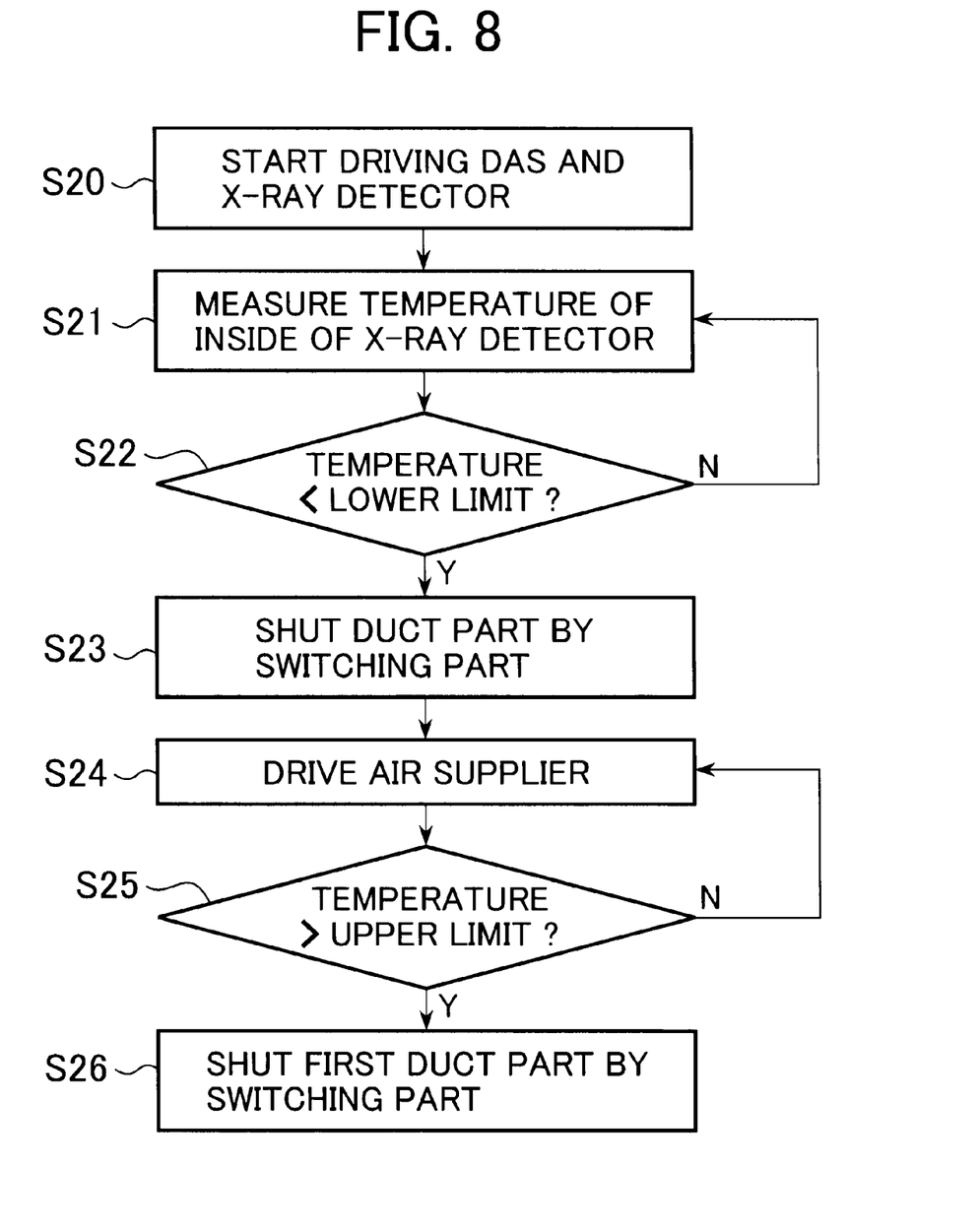
FIG. 8 is a flowchart showing an overview of a processing according to the second embodiment.

Next, using FIG. 6 through FIG. 8, the second embodiment is described. In addition, a detailed description of the configuration common with the first embodiment is omitted.

As shown in FIG. 6 and FIG. 7, this embodiment is similar to the configuration in the first embodiment except for the configuration of the air supplier 121 and having a pathway 120 and a duct 120a.

The pathway 120 is configured so that it communicates between the X-ray detector 113 and the DAS 118 and is capable of leading the air from the DAS 118 to the X-ray detector 113.

The duct 120a is configured so that it communicates between the inside of the DAS 118 and the outside of the DAS 118 and is capable of exhausting the air from the DAS 118 out of the DAS 118.

In addition, a wall 120c is installed between the pathway 120 and the duct 120a, which are isolated from each other.

As shown in FIG. 7, the air supplier 121 has a switching part 121a. The switching part 121a has a fan part 121b having a blade shape, an adjustment member 121c consisting of crescent shaped dividers installed on the front face or the back face of the fan part 121b, and a motor (not shown) that rotationally drives the adjustment member 121c.

The fan part 121b has a function to supply the air in the DAS 118 to the X-ray detector 113 via the pathway 120 or exhaust the air out of the DAS 118 via the duct 120a.

The adjustment member 121c has a function to adjust the communication state of the pathway 120 and the duct 120a relative to the DAS 118 in order to allow the air from inside of the DAS 118 to be supplied to the pathway 120 or the duct 120a. For example, as in FIG. 7, when the straight portion of the adjustment member 121c and the wall 120c intersect, it is also possible to supply a portion of the air from inside of the DAS 118 to the pathway 120 and supply the rest of the air to the duct 120a.

Here, the "communication state" represents the placement state of the adjustment member 121c for supplying the air from the DAS 118 to only one of the pathway 120 and the duct 120a, or supplying the air to both at a predefined rate.

The controller 125 drives the fan part 121b so as to supply the air in the DAS 118 to the X-ray detector 113 via the pathway 120, or so as to exhaust the air out of the DAS 118 via the duct 120a. Moreover, the controller 125 drives the motor, which is not shown. With the motor driven, the adjustment member 121c performs the operation to switch the communication state between the DAS 118, and the pathway 120 and the duct 120a.

Next, using FIG. 8, the operation of this embodiment is described in detail.

First, in conjunction with use of the X-ray CT apparatus, the X-ray detector 113 and the DAS 118 start to operate (S20).

The DAS 118 radiates heat as it is driven. The air in the DAS 118 is warmed with this heat.

On the other hand, in conjunction with the operation of the X-ray detector 113, the temperature measuring part 123 starts to measure the temperature in the X-ray detector 113 (S21). The temperature measuring part 123, for example, performs measurements at predetermined time intervals.

Here, if the measured temperature by the temperature measuring part 123 is below the lower limit (for example, 24° C.) (that is, if it is "Y" at S22), the controller 125 sends a drive signal to the switching part 121a (motor that drives the adjustment member 121c).

Based on this drive signal, the switching part 121a (adjustment member 121c and motor) performs the operation to block the duct 120a (S23).

If the measured temperature at the temperature measuring part 123 is equal to or above the lower limit (if it is N at S22), no drive signal is sent to the switching part 121a by the controller 125.

After the switching part 121a (adjustment member 121c) blocks the duct 120a at S23, the air supplier 121 is driven by the drive signal from the controller 125. Then, the warmed air in the DAS 118 is supplied, by the air supplier 121, to the X-ray detector 113 via the pathway 120 (S24). In addition, S23 and S24 need not be performed in this order, and if it is Y at S22, for example, these may be performed simultaneously by the drive signal from the controller 125.

Under the state in which the air supplier 121 is driven and the warmed air in the DAS 118 is supplied into the X-ray detector 113 at S24, if the measured temperature by the temperature measuring part 123 exceeds the upper limit (that is, if it is "Y" at S25), the controller 125 sends a drive signal to the switching part 121a.

If the measured temperature at the temperature measuring part 123 does not exceed the upper limit (if it is N at S25), no drive signal is sent to the switching part 121a by the controller 125.

Based on the drive signal in the case of Y at S25, the switching part 121a (adjustment member 121c) performs an operation to block the pathway 120 (S26). In this case, the duct 120a and the inside of the DAS 118 are in communication. Therefore, with the operation of the air supplier 121, the air in the DAS 118 is exhausted out of the DAS 118 through the duct 120b.

As above, according to this embodiment, in addition to the effect of the first embodiment, an effect that also allows temperature control in the DAS 118 results.

In addition, although this embodiment is configured with the air regulator 122 installed, with the configuration of the switching part 121a and the duct 120a as mentioned above, it is possible to exhaust the warmed air in the DAS 118 out of the DAS 118. Therefore, the air regulator 122 need not be installed.

[The Third Embodiment]

Figure 9:
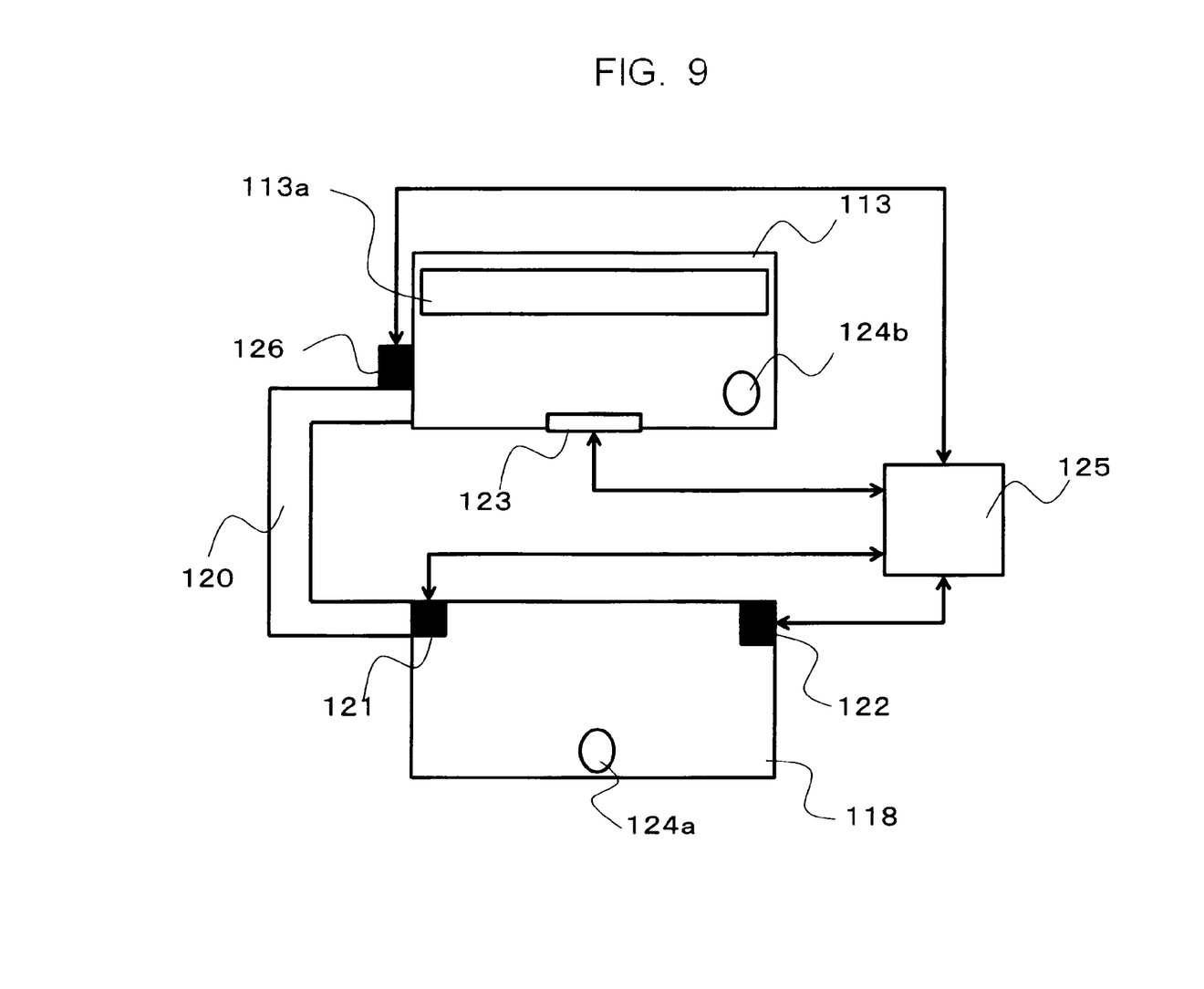
FIG. 9 is a block diagram showing the relation between components of the X-ray CT apparatus according to the third embodiment.
Figure 10:
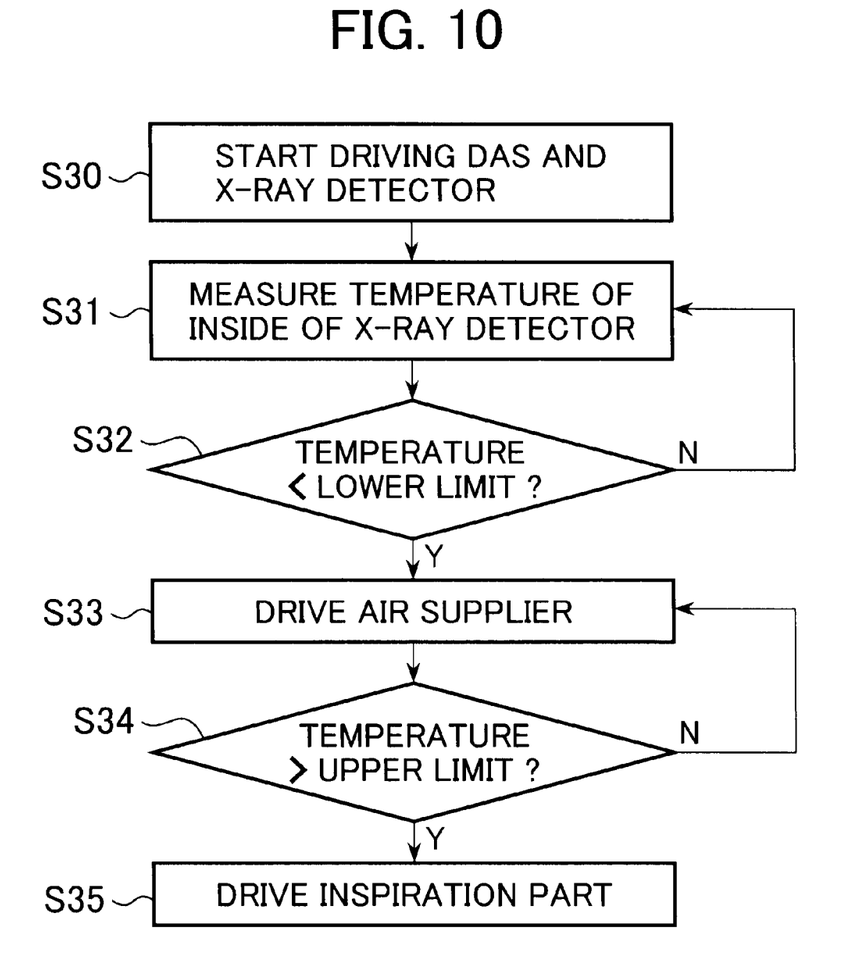
FIG. 10 is a flowchart showing an overview of a processing according to the third embodiment.

Next, using FIG. 9 through FIG. 10, the third embodiment is described. In addition, for the configuration similar to the first embodiment, a detailed description is omitted.

As in FIG. 9, in this embodiment, an inspiration part 126 for inspiring the air outside the X-ray detector 113 into the X-ray detector 113 is installed.

The inspiration part 126 performs the operation to inspire the air outside the X-ray detector 113 into the X-ray detector 113 based on a drive signal from the controller 125. For this purpose, the inspiration part 126 is configured to include a fan, for example.

Next, using FIG. 10, the operation of this embodiment is described in detail.

First, in conjunction with use of the X-ray CT apparatus, the X-ray detector 113 and the DAS 118 start to operate (S30).

The DAS 118 radiates heat as it is driven. The air in the DAS 118 is warmed with this heat.

On the other hand, in conjunction with the operation of the X-ray detector 113, the temperature measuring part 123 starts to measure the temperature in the X-ray detector 113 (S31). The temperature measuring part 123, for example, performs measurements at predetermined time intervals.

Here, if the measured temperature by the temperature measuring part 123 is below the lower limit (for example, 24° C.) (that is, if it is "Y" at S32), the controller 125 sends a drive signal to the air supplier 121.

Based on this drive signal, the air supplier 121 supplies the warmed air in the DAS 118 to the X-ray detector 113 via the pathway 120 (S33).

If the measured temperature at the temperature measuring part 123 is equal to or above the lower limit (if it is N at S32), no drive signal is sent to the air supplier 121 by the controller 125.

Under the state in which the air supplier 121 is driven and the warmed air in the DAS 118 is supplied into the X-ray detector 113 at S33, if the measured temperature by the temperature measuring part 123 exceeds the upper limit (that is, if it is "Y" at S34), the controller 125 sends a drive signal to the inspiration part 126.

If the measured temperature at the temperature measuring part 123 does not exceed the upper limit (if it is N at S34), no drive signal is sent to the inspiration part 126 by the controller 125.

Based on this drive signal, the inspiration part 126 supplies the air from the outside of the X-ray detector 113 into the X-ray detector (S35).

As above, according to this embodiment, not only the air warmed in the DAS 118 but also cool air outside the X-ray detector 113 can be supplied into the X-ray detector 113. Therefore, it is easier to perform temperature control in the X-ray detector 113 than the first embodiment. In addition, also in this embodiment, the configuration of the air regulator 122 is not essential.

[Items that are Common to the First Through Third Embodiments]

In the description of the first through third embodiments, a configuration has been described that leads the air warmed at the DAS 118 to the X-ray detector 113. In general, in the X-ray CT apparatus, the DAS 118 is installed near the X-ray detector 113. Therefore, by installing the pathway 120 as in this embodiment, the path length can be shortened, an attempting at compactness. Moreover, there is a benefit in that there is less heat loss due to the path. Furthermore, there is a benefit that control with the controller 125 is easy because the DAS 118 and the X-ray detector 113 are simultaneously driven.

Continuing to operate the X-ray CT apparatus while stopping the air-supply operation will raise the temperature in the DAS 118. In this case, for example, if the controller 125 sends a stop drive signal to the air supplier 121, it is conceivable that a drive signal could be sent so as to cause the air regulator 122 to perform the exhaust operation at the same time. In addition, it is of course possible to drive the air supplier 121 and the air regulator 122 simultaneously.

In this case, the air-supply operation of the air supplier 121 and/or the exhaust operation of the air regulator 122 will distribute the air from the vent 124a into the DAS 118, so the cooling effect in the DAS 118 can be enhanced.

Furthermore, another temperature measuring part (DAS-side temperature measuring part) is installed also in the DAS 118, so that the measured result from this temperature measuring part and the measured result from the temperature measuring part 123 may be combined to perform operational control of the air supplier 121, the switching part 121a, the air regulator 122, etc. Performing such control allows temperature control coupled with the temperature, both in the X-ray detector 113 and in the DAS 118.

[The Fourth Embodiment]

Figure 11:
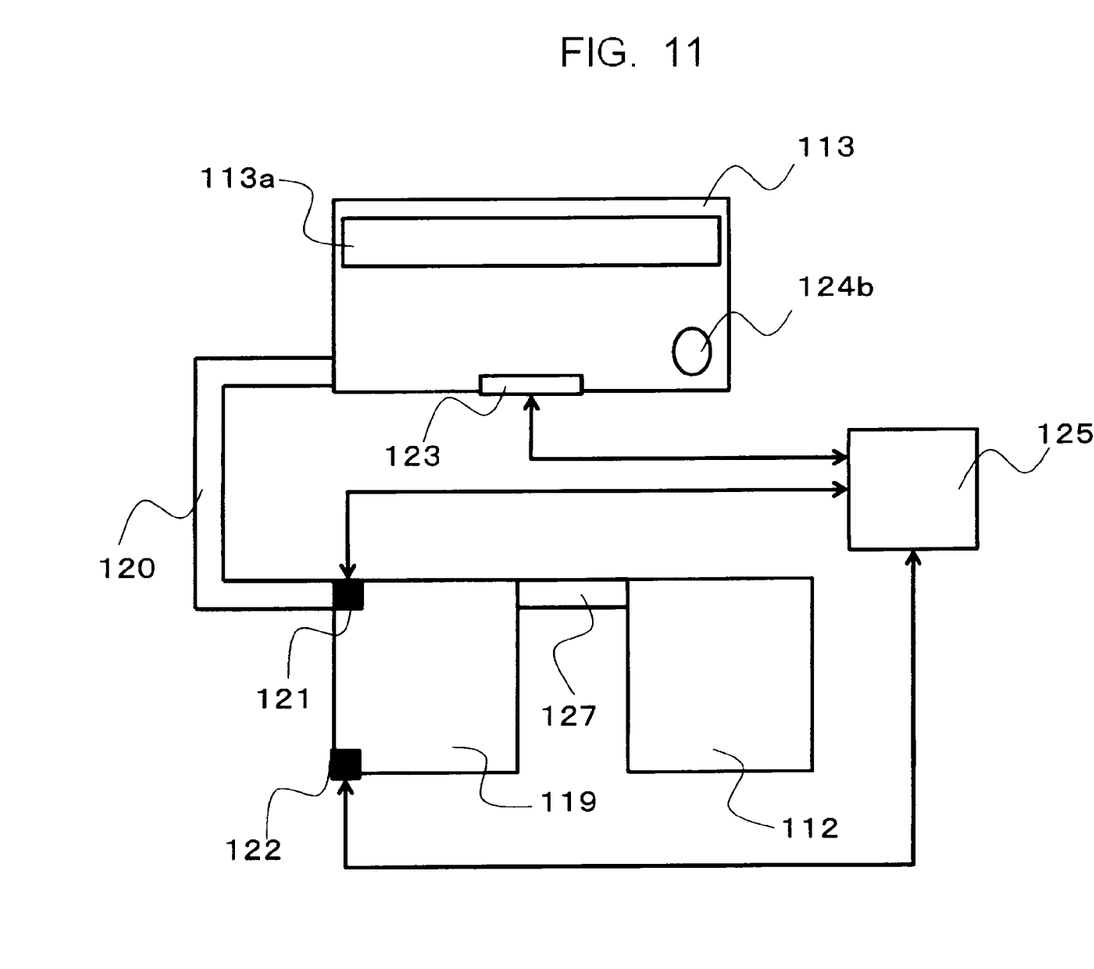
FIG. 11 is a block diagram showing the relation between components of the X-ray CT apparatus according to the fourth embodiment.
Figure 12:
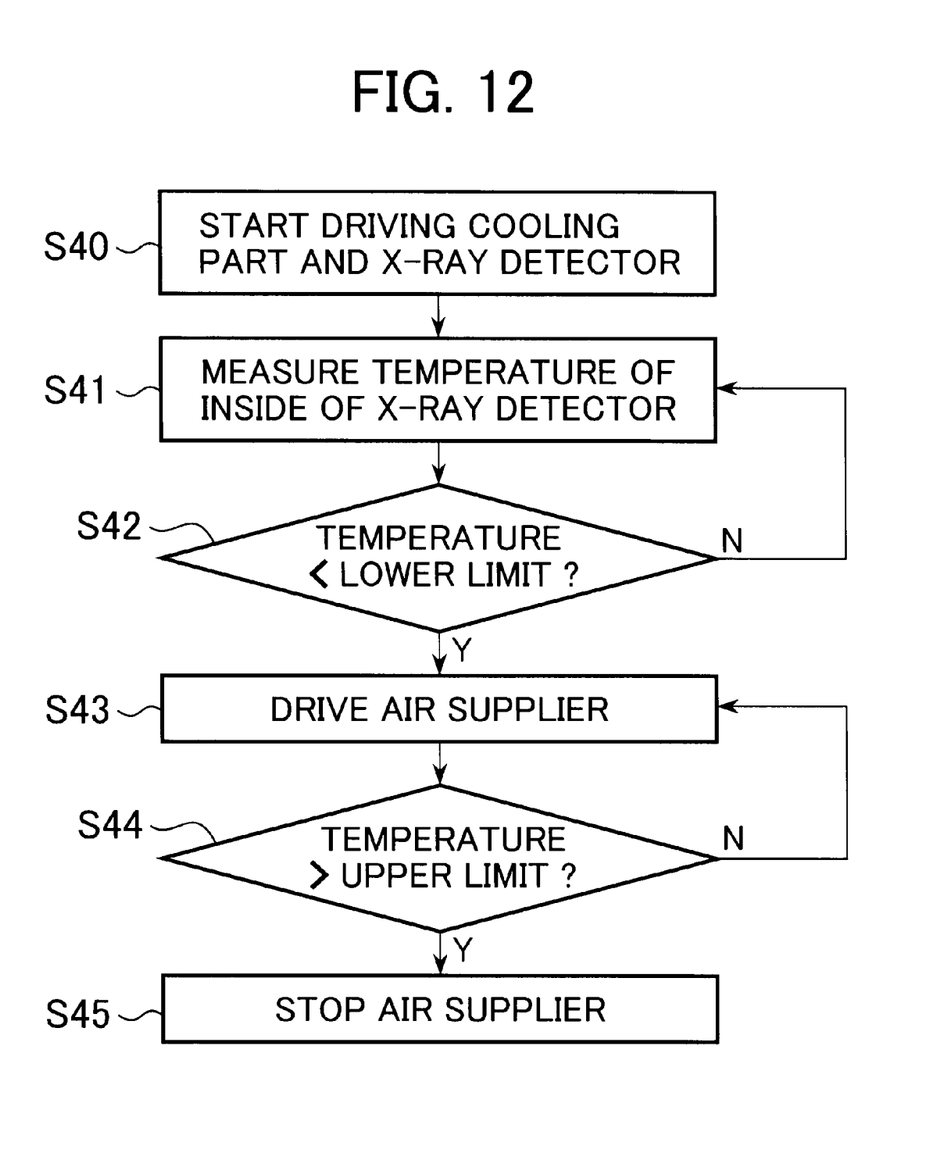
FIG. 12 is a flowchart showing an overview of a processing according to the fourth embodiment.

Next, using FIG. 11 and FIG. 12, the fourth embodiment is described. In addition, for the configuration similar to the first embodiment, a detailed description is omitted.

When X-rays are generated at the X-ray generator 112, in conjunction with that operation, the air in the X-ray generator 112 is warmed. Thus, the cooling part 119 for cooling the inside of the X-ray generator 112 is installed. The X-ray generator 112 is cooled by supplying air from the cooling part 119 with oil and the like circulated in the X-ray generator 112 and cooling part 119. On the other hand, with the heat generated in conjunction with the air-supply operation of the cooling part 119, the air in the cooling part 119 is warmed.

In this embodiment, a configuration to make temperature adjustments of inside of the X-ray detector 113 using the air warmed in the cooling part 119 but not the air warmed in the DAS 118 is described.

In this embodiment, the cooling part 119 is in communication with the X-ray detector 113 via the pathway 120. Moreover, the cooling part 119 is in communication with the X-ray generator 112 via the communication part 127.

As above, the cooling part 119 supplies the air to the X-ray generator 112 via the communication part 127 and cools the X-ray generator 112.

On the other hand, the air in the cooling part 119 that is warmed by heat generated as the air is supplied from the cooling part 119 is supplied to the X-ray detector 113 via the pathway 120 by driving the air supplier 121.

In addition, as a result of the drive of the X-ray generator 112, the cooling part 119 is required to supply air constantly in order to cool the X-ray generator 112. Thus, if the air warmed in the cooling part 119 is not supplied to the X-ray detector 113, the temperature in the cooling part 119 rises. Therefore, in this embodiment, the air regulator 122 is installed in the cooling part 119. The air regulator 122 has a function to exhaust the air in the cooling part 119 out of the cooling part 119 or inspire the air outside the cooling part 119 into the cooling part 119 in order to make temperature adjustments in the cooling part 119.

Next, using FIG. 12, the operation of this embodiment is described in detail.

First, in conjunction with use of the X-ray CT apparatus, the X-ray detector 113 and the cooling part 119 start to operate (S40).

The cooling part 119 generates heat as it is driven. The air in the cooling part 119 is warmed with this heat.

On the other hand, in conjunction with the operation of the X-ray detector 113, the temperature measuring part 123 starts to measure the temperature in the X-ray detector 113 (S41). The temperature measuring part 123, for example, performs measurements at predetermined time intervals.

Here, if the measured temperature by the temperature measuring part 123 is below the lower limit (for example, 24° C.) (if it is Y at S42), the controller 125 sends a drive signal to the air supplier 121.

Based on this drive signal, the air supplier 121 is driven and supplies the warmed air in the cooling part 119 to the X-ray detector 113 via the pathway 120 (S43).

If the measured temperature at the temperature measuring part 123 is equal to or below the lower limit (if it is N at S42), no drive signal is sent to the air supplier 121 by the controller 125.

If the measured temperature at the temperature measuring part 123 exceeds the upper limit, with the air supplier 121 driven and the warmed air in the cooling part 119 supplied into the X-ray detector 113 at S43 (if it is Y at S44), the controller 125 sends a stop drive signal to the air supplier 121.

In addition, if the measured temperature at the temperature measuring part 123 does not exceed the upper limit (if it is N at S44), no stop drive signal is sent to the air supplier 121 by the controller 125.

Based on this stop drive signal, the air supplier 121 stops the operation to supply the air to the X-ray detector 113 (S45). In addition, if the air supplier 121 is provided with a fan, for example, it is also possible to allow such an operation as reducing the revolution speed of the fan without having to completely stop its operation.

As above, according to this embodiment, without installing a warming means such as a heater in the X-ray detector 113, the air warmed in the cooling part 119 allows temperature adjustment in the X-ray detector 113. Therefore, no noise is added to the detection result from the X-ray detector 113 due to the effect of electromagnetic waves generated by the operation of the warming means. That is, the image quality of tomographic images and volume images formed using that detection result is not affected.

[Variations]

If there is air warmed by heat generation in the X-ray CT apparatus not limited to the DAS 118 and the cooling part 119, leading the air to the X-ray detector 113 via the pathway 120 allows temperature control of the X-ray detector 113.

It is also possible to cause both the DAS 118 and the cooling part 119 to communicate with the X-ray detector 113 via pathways and perform temperature control of the X-ray detector 113 based on the air warmed by respective drives.

It is also possible to install a heater in the X-ray detector 113 and perform warming with the heater only if the X-ray detector 113 is not driven. In that case, after starting the apparatus, the temperature in the X-ray detector 113 can be quickly increased to a predefined temperature. Therefore, it is also possible to obtain the effect of improving the examination efficiency.

Other than the heater, for example, by using heat at the time of warm-up of the X-ray generator (X-ray tube), the temperature in the X-ray detector 113 can be quickly increased to a predefined temperature.

Moreover, although in the first through fourth embodiments, the upper limit and lower limit of the temperature in the X-ray detector 113 are measured separately by the temperature measuring part 123, whether it is within the acceptable range or not (for example, whether it is within the range of 25° C.±1° C. or not) is measured, and operation control of each configuration may be performed based on the result thereof. In this case, it is possible to attempt to simplify processing with the controller 125.

Furthermore, although in the first through fourth embodiments, the flow of the processing is to first determine the lower limit in the X-ray detector 113, depending on the state that the X-ray CT apparatus is in, the flow may be to first determine the upper limit.

It is also possible to install the pathway 120 and the duct 120*a* in the second embodiment in the cooling part 119 and perform control similar to that in the second embodiment.

As above, according to the embodiments described, temperature control of the X-ray detector can be performed without using a warming such as a heater.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising a rotation base that has a plurality of units, including an X-ray generator that irradiates a subject with X-rays, and an X-ray detector that detects X-rays transmitted through said subject, the X-ray CT apparatus comprising:
   a pathway that communicates between said X-ray detector and at least one other unit excluding said X-ray generator and said X-ray detector;
   an air supplier that supplies air in said other units to said X-ray detector via said pathway;
   an air regulator configured to exhaust air out of said other units and/or inspire air outside said other units into said other units;
   a temperature measuring part that measures the temperature in said X-ray detector; and
   a controller that performs control of said air supplier and said air regulator based on the measured result from said temperature measuring part.

2. An X-ray CT apparatus comprising an X-ray generator that irradiates a subject with X-rays, and an X-ray detector that detects X-rays transmitted through said subject, the X-ray CT apparatus comprising:
   a data acquisition system that acquires detected data from said X-ray detector;
   a pathway that communicates between said data acquisition system and said X-ray detector;
   an air supplier that supplies air in said data acquisition system to said X-ray detector via said pathway;
   an air regulator configured to exhaust air out of said data acquisition system and/or inspire air outside said data acquisition system into said data acquisition system;
   a temperature measuring part that measures the temperature in said X-ray detector; and
   a controller that performs control of said air supplier and said air regulator based on the measured result from said temperature measuring part.

3. The X-ray CT apparatus according to claim 2, further comprising:
   a duct that communicates between said data acquisition system and outside of said data acquisition system; and
   a switching part that switches the destination of air so that the air from said data acquisition system supplied by said air supplier is flowed into said pathway or said duct;

wherein said controller performs control to drive said switching part based on the measured result from said temperature measuring part.

4. An X-ray CT apparatus comprising an X-ray generator that irradiates a subject with X-rays, and an X-ray detector that detects X-rays transmitted through said subject, the X-ray CT apparatus comprising:
   a cooling part that cools said X-ray generator;
   a pathway that communicates between said cooling part and said X-ray detector;
   an air supplier that supplies air exhausted from said cooling part to the X-ray detector via the pathway;
   an air regulator configured to exhaust air out of said cooling part and/or inspire air outside said cooling part into said cooling part;
   a temperature measuring part that measures the temperature in the X-ray detector; and
   a controller that performs control of said air supplier and said air regulator based on the measured result from said temperature measuring part.

5. The X-ray CT apparatus according to claim 4, further comprising:
   a duct that communicates between said cooling part and outside of said cooling part; and
   a switching part that switches the destination of air so that the air from said cooling part supplied by said air supplier is flowed into said pathway or said duct;
   wherein said controller performs control to drive said switching part based on the measured result from said temperature measuring part.

6. The X-ray CT apparatus according to any of claims 1, 2, and 4 further comprising:
   an inspiration part that inspires the air outside said X-ray detector into said X-ray detector;
   wherein said controller performs control to drive said inspiration part based on the measured result from said temperature measuring part.

* * * * *